United States Patent
Suzuki et al.

(10) Patent No.: US 9,775,685 B2
(45) Date of Patent: Oct. 3, 2017

(54) DENTAL SYRINGE

(71) Applicant: GC Corporation, Tokyo (JP)

(72) Inventors: Fumiko Suzuki, Tokyo (JP); Tatsunosuke Miyano, Tokyo (JP)

(73) Assignee: GC Corporation, Tokyo (JP)

( * ) Notice: Subject to any disclaimer, the term of this patent is extended or adjusted under 35 U.S.C. 154(b) by 8 days.

(21) Appl. No.: 14/427,662

(22) PCT Filed: Sep. 11, 2013

(86) PCT No.: PCT/JP2013/074469
§ 371 (c)(1),
(2) Date: Mar. 12, 2015

(87) PCT Pub. No.: WO2014/050550
PCT Pub. Date: Apr. 3, 2014

(65) Prior Publication Data
US 2015/0342705 A1     Dec. 3, 2015

(30) Foreign Application Priority Data
Sep. 28, 2012   (JP) .................. 2012-216898

(51) Int. Cl.
A61C 5/04       (2006.01)
A61C 5/06       (2006.01)
A61C 5/62       (2017.01)

(52) U.S. Cl.
CPC ................ *A61C 5/062* (2013.01); *A61C 5/62* (2017.02)

(58) Field of Classification Search
CPC ........... A61C 5/062; A61M 2005/3118; A61M 2005/3123; A61M 2005/3131;
(Continued)

(56) References Cited

U.S. PATENT DOCUMENTS

| | | |
|---|---|---|
| 5,181,918 A | 1/1993 | Brandhorst et al. |
| 5,395,326 A | 3/1995 | Haber et al. |

(Continued)

FOREIGN PATENT DOCUMENTS

| | | |
|---|---|---|
| FR | 1053583 | 2/1954 |
| FR | 1108413 | 1/1956 |

(Continued)

OTHER PUBLICATIONS

International Search Report dated Oct. 8, 2013.

*Primary Examiner* — Cris L Rodriguez
*Assistant Examiner* — Mirayda A Aponte
(74) *Attorney, Agent, or Firm* — IPUSA, PLLC

(57) ABSTRACT

A dental syringe that facilitates the expulsion of air from a syringe body when dental material is injected into the syringe body from a discharge port of the syringe body and the discharge of the dental material from the syringe body during use for treatment. The syringe includes a syringe body, a plunger, and an O-ring that is mounted in an engagement groove formed at a front end portion of the plunger. The engagement groove includes a shallow groove at the front end side and a deep groove at the rear end side. When the dental material is injected into the syringe body, the O-ring engages with the shallow groove, and when discharging the dental material, the O-ring engages with the deep groove.

2 Claims, 3 Drawing Sheets

(58) Field of Classification Search
CPC ...... A61M 2005/31508; A61M 5/3148; A61M 5/3146; A61M 5/315; A61M 5/31501; A61M 5/31513; A61M 5/31505; A61M 5/24; A61M 5/31511; A61M 5/31508; A61M 5/00; A61M 5/31515; G09B 23/28; G09B 23/285
USPC .............. 433/90; 604/513, 167.06, 539, 110, 604/181–235; 434/262–275
See application file for complete search history.

(56) References Cited

U.S. PATENT DOCUMENTS

| | | | |
|---|---|---|---|
| 5,549,573 | A | 8/1996 | Waskonig |
| 2009/0047622 | A1* | 2/2009 | Leiner .................. A61C 5/062 433/90 |
| 2009/0289084 | A1 | 11/2009 | Kunishi et al. |

FOREIGN PATENT DOCUMENTS

| | | |
|---|---|---|
| JP | H04-244164 | 9/1992 |
| JP | H07-506508 | 7/1995 |
| JP | 2001-057987 | 3/2001 |
| JP | 2008-018061 | 1/2008 |
| JP | 2008-018351 | 1/2008 |
| JP | 2008-018974 | 1/2008 |
| JP | 2009-011341 | 1/2009 |
| JP | 2009011341 A * | 1/2009 |
| JP | 2011-004775 | 1/2011 |
| JP | 2013-164109 | 8/2013 |
| WO | 95/23622 | 9/1995 |
| WO | 2010/126536 | 11/2010 |

\* cited by examiner

DENTAL SYRINGE

TECHNICAL FIELD

The present invention relates to a dental syringe that has dental material pre-injected from a discharge port of a syringe body and is used in such a state. The present invention further relates to a dental syringe that enables easy discharge of air within the syringe body to the exterior while injecting the dental material into the syringe body and easy discharge of the dental material that has been injected into the syringe body during use for treatment.

BACKGROUND ART

In dental syringes that have dental material with a relatively low viscosity such as dental adhesive or low-fluidity composite resin pre-injected therein to be used in such a state, the dental material may often be injected from a discharge port of a syringe body.

When the dental material is injected, air inevitably remains within the syringe body, and as a result, there may be cases where a defined amount of dental material cannot be injected, or a desired amount of dental material cannot be discharged during actual use of the dental syringe, for example.

In view of such a problem concerning residual air within the syringe body, an ejector that is configured to discharge residual air within an injection chamber is known, the ejector including a cylinder member having a fluid ejection port formed at its front end, a plunger member, an annular concave groove that is formed at an outer periphery of the plunger member near its front end, and a sealing O-ring that is mounted at the bottom face of the annular concave groove. An air release passage is formed at the bottom face of the annular concave groove, and the annular concave groove is arranged to extend below the O-ring at a position where the O-ring comes close to the rear face of the annular concave groove. When the air pressure within the injection chamber increases at a position where the O-ring comes into contact with the rear face of the annular concave groove, the sealed state between the O-ring and the rear face is released via the air release passage and air within the injection chamber is discharged (see e.g., Patent Document 1).

The above ejector (syringe) is configured to discharge residual air to the exterior by including an air release passage. However, in practice, merely including such an air release passage may not be adequate for discharging residual air (see e.g., paragraph 0022 and FIG. 6 of Patent Document 1). Upon injecting dental restorative paste or the like (dental material) from the ejection port (discharge port), residual air is pushed by the dental restorative paste or the like (dental material) toward the O-ring (plunger) to increase the internal pressure (see e.g., paragraph 0022 of Patent Document 1), but this merely causes the plunger to be pushed toward the opposite side of the ejection port (discharge port). That is, the residual air remains sealed within the ejector (syringe).

Accordingly, in the above ejector (syringe), the rear end of the plunger is pushed by a "push plate" to fix the plunger in place so that the plunger would not move even if it were pushed by the residual air, and the air pressure within the injection chamber is increased to prompt the O-ring to move and release the sealed state between the O-ring and the annular concave groove so that the residual air can be discharged (see e.g., paragraph 0023 and FIG. 7 of Patent Document 1).

In the above ejector (syringe), the rear end of the plunger has to be pushed by the "push plate" until the residual air is discharged from the syringe, and the "plush plate" has to be removed around the time the residual air has been discharged. If the "push plate" is removed too early, the residual air may not be completely discharged. On the other hand, if the "push plate" is removed too late, the dental restorative paste or the like (dental material) may leak from the air release passage, for example. Thus, the above ejector is extremely difficult to handle.

Also, when air remains within the syringe body, even when the plunger ceases to be pushed to stop the discharge of dental material, the residual air that has been compressed up to this point may expand and push the dental material within the syringe body to cause leakage of the dental material from the discharge port of the syringe body.

In view of the problem concerning the leakage of dental material from the nozzle (discharge port) as described above, an extruding structure for a dental viscous material container having a circular internal cross-section with a uniform diameter, a nozzle arranged at its front end, and an opening arranged at its rear end is known. The extruding structure includes a moving cap that may be moved by a plunger that is inserted from the rear end of the container for pushing dental viscous material contained within the container toward the nozzle side, or an extrusion piston to which the container body is mounted. The moving cap includes a portion at the nozzle side that has a smaller diameter than the interior of the container, and an O-ring mounting groove extending from this portion into which an O-ring is mounted. The O-ring mounting groove is arranged such that a clearance between its bottom part and an inner face of the container body does not change or gets narrower, continuously or stepwise, from the nozzle side toward the opposite side (see e.g., Patent Document 2).

In the above dental viscous material container, the O-ring mounting groove is arranged such that the clearance between its bottom part and an inner face of the container body does not change or gets narrower, continuously or stepwise, from the nozzle side toward the opposite side. Accordingly, particularly in the case where the clearance gets narrower, when the plunger is pushed toward the nozzle side, the O-ring is positioned within a narrow gap and a large load is applied when the plunger is pushed toward the nozzle side, and as a result, when the plunger ceases to be pushed toward the nozzle side, the plunger moves toward the opposite side of the nozzle to reduce the load. Thus, even if the volume of residual air expands, a space within the container body (syringe body) corresponding to the amount of expansion of the residual air may be secured and the dental material may be prevented from leaking.

However, by arranging a large load to be applied upon pushing the plunger toward the nozzle side, a large force may be required upon ejecting a relatively low-viscosity dental material at the time of actual treatment, for example. Thus, the above dental viscous material container is difficult to handle, and it may be hard to discharge a precise amount of material owing to a difficulty in adjusting the force to be applied.

PRIOR ART DOCUMENTS

Patent Documents

Patent Document 1: Japanese Laid-Open Patent Publication No. 2011-4775

Patent Document 2: Japanese Laid-Open Patent Publication No. 2001-57987

SUMMARY OF THE INVENTION

Problem to be Solved by the Invention

The present invention has been conceived in view of the foregoing problems associated with the prior art, and it is an object of the present invention to provide a dental syringe that enables easy discharge of air within a syringe body to the exterior while injecting dental material into the syringe body from a discharge port of the syringe body and easy discharge of the dental material that has been injected into the syringe body during use for treatment.

Means for Solving the Problem

The present inventors have conducted extensive investigations to solve the above problems and have found that certain advantageous effects may be obtained by implementing the following features in a dental syringe in which dental material is to be injected into its syringe body from a discharge port. The dental syringe includes the syringe body having the discharge port arranged at a front end and a plunger insertion port arranged at a rear end, a plunger to be inserted into the syringe body from the plunger insertion port, and an O-ring to be mounted in an engagement groove formed along a circumferential direction of a front end portion of the plunger, the O-ring being held in contact with an outer face of the engagement groove and an inner face of the syringe body. The engagement groove of the plunger includes a shallow groove arranged at a front end side and a deep groove arranged at a rear end side. The shallow groove is arranged such that when the dental material starts being injected into the syringe body from the discharge port and the plunger is moved toward the rear end side, the O-ring stops the plunger from moving within the syringe body; and after air is discharged toward the rear end side of the syringe body from a gap formed between the O-ring and the syringe body and/or a gap formed between the O-ring and the plunger, the O-ring is held in contact with the inner face of the syringe body with a strength that allows the plunger to be pushed and moved along with the O-ring toward the rear end side by the dental material injected from the discharge port of the syringe body. When an end portion at the rear end side of the plunger is pushed by a finger to discharge the dental material injected into the syringe body from the discharge port of the syringe body, the O-ring is moved from the shallow groove to the deep groove.

The present inventors have found that by implementing the above features, the following advantageous effects can be obtained. When dental material is injected from the discharge port, the plunger pushed by residual air is urged to move toward the opposite side of the discharge port. However, the O-ring that is held in contact with the outer face of the engagement grove and the inner face of the syringe body resists movement, and as a result, the O-ring is arranged in the "shallow groove" positioned relatively toward the front end side of the engagement groove of the plunger. At this position, the O-ring is tightly held between the outer face of the engagement groove and the inner face of the syringe body, and as a result, a large load is applied to the plunger that is held in contact with the O-ring such that the movement of the plunger is restricted. While the movement of the plunger is decelerated or stopped due to the above restriction, residual air may be discharged toward the rear end side of the syringe body through gaps formed at the O-ring, for example. After the residual air is discharged, the dental material may flow directly toward the front end side of the plunger to push the plunger along with the O-ring toward the rear end side. In this way, residual air may be reliably discharged and dental material may be easily injected in such a state. Further, during treatment, when the plunger is pushed to discharge the dental material and the plunger moves toward the discharge port, the O-ring that is held in contact with the outer face of the engagement groove and the inner face of the syringe body resists movement. As a result, the O-ring is arranged in the "deep groove" positioned relatively toward the rear end side of the engagement groove of the plunger. At such position, the O-ring is more loosely held between the outer face of the engagement groove and the inner face of the syringe body, and as a result, a large load is not applied to the plunger that is held in contact with the O-ring. Thus, the dental material may be easily discharged. Also, even if the required load upon discharging the dental material is reduced as described above, because residual air is not present, leakage of the dental material due to residual air may be avoided.

Thus, an aspect of the present invention is directed to a dental syringe in which dental material is to be injected into a syringe body from a discharge port. The dental syringe includes the syringe body having the discharge port arranged at a front end and a plunger insertion port arranged at a rear end, a plunger to be inserted into the syringe body from the plunger insertion port, and an O-ring to be mounted in an engagement groove formed along a circumferential direction of a front end portion of the plunger, the O-ring being held in contact with an outer face of the engagement groove and an inner face of the syringe body. The engagement groove of the plunger includes a shallow groove arranged at a front end side and a deep groove arranged at a rear end side, such that a perimeter of the plunger at the deep groove portion is smaller than the perimeter of the plunger at the shallow groove portion. The shallow groove is arranged such that when the dental material starts being injected into the syringe body from the discharge port of the syringe body and the plunger is moved toward the rear end side, the O-ring stops the plunger from moving within the syringe body; and after air is discharged toward the rear end side of the syringe body from a gap formed between the O-ring and the syringe body and/or a gap formed between the O- ring and the plunger, the O-ring is held in contact with the inner face of the syringe body with a strength that allows the plunger to be pushed and moved along with the O-ring toward the rear end side by the dental material injected from the discharge port of the syringe body. When an end portion at the rear end side of the plunger is pushed by a finger to discharge the dental material injected into the syringe body from the discharge port of the syringe body, the O-ring is moved from the shallow groove to the deep groove.

Advantageous Effects of the Invention

According to an aspect of the present invention, a dental syringe in which dental material is to be injected into a syringe body from a discharge port includes the syringe body having the discharge port arranged at a front end and a plunger insertion port arranged at a rear end, a plunger to be inserted into the syringe body from the plunger insertion port, and an O-ring to be mounted in an engagement groove formed along a circumferential direction of a front end portion of the plunger, the O-ring being held in contact with an outer face of the engagement groove and an inner face of the syringe body. The engagement groove of the plunger includes a shallow groove arranged at a front end side and a deep groove arranged at a rear end side. The shallow groove is arranged such that when the dental material starts being injected into the syringe body from the discharge port of the syringe body and the plunger is moved toward the rear end side, the O-ring stops the plunger and restricts its movement within the syringe body; and after residual air is discharged toward the rear end side of the syringe body from a gap formed between the O-ring and the syringe body and/or a gap formed between the O-ring and the plunger, the O-ring is held in contact with the inner face of the syringe body with a strength that allows the plunger to be pushed by the dental material injected from the discharge port of the syringe body and moved along with the O-ring toward the rear end side. When an end portion at the rear end side of the plunger is pushed by a finger to discharge the dental material injected into the syringe body from the discharge port of the syringe body, the O-ring is moved from the shallow groove to the deep groove.

By implementing such features, when dental material is injected from the discharge port, the plunger pushed by residual air is urged to move toward the opposite side of the discharge port. However, the O-ring that is held in contact with the outer face of the engagement grove and the inner face of the syringe body resists movement, and as a result, the O-ring is arranged in the "shallow groove" positioned relatively toward the front end side of the engagement groove of the plunger. At this position, the O-ring is tightly held between the outer face of the engagement groove and the inner face of the syringe body, and as a result, a large load is applied to the plunger that is held in contact with the O-ring such that the movement of the plunger is restricted. While the movement of the plunger is decelerated or stopped due to the above restriction, residual air may be discharged toward the rear end side of the syringe body through gaps formed at the O-ring, for example. After the residual air is discharged, the dental material may flow directly toward the front end side of the plunger to push the plunger along with the O-ring toward the rear end side. In this way, residual air may be reliably discharged and dental material may be easily injected in such a state. Further, during treatment, when the plunger is pushed to discharge the dental material and the plunger moves toward the discharge port, the O-ring that is held in contact with the outer face of the engagement groove and the inner face of the syringe body resists movement. As a result, the O-ring is arranged in the "deep groove" positioned relatively toward the rear end side of the engagement groove of the plunger. At such position, the O-ring is more loosely held between the outer face of the engagement groove and the inner face of the syringe body, and as a result, a large load is not applied to the plunger that is held in contact with the O-ring. Thus, the dental material may be easily discharged. Also, even if the required load upon discharging the dental material is reduced as described above, because residual air is not present, leakage of the dental material due to residual air may be avoided.

EMBODIMENTS FOR IMPLEMENTING THE INVENTION

Figure 1:
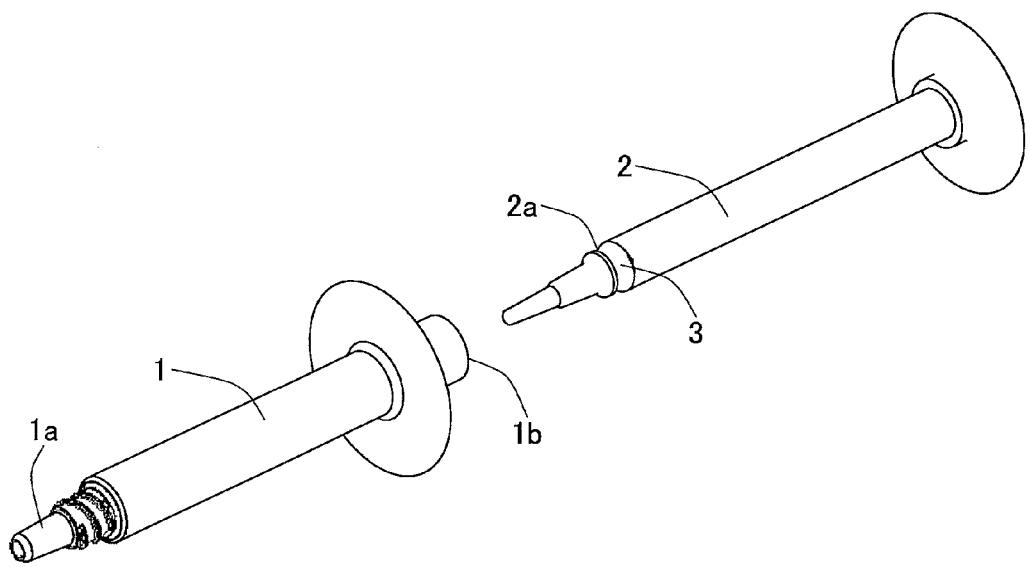
FIG. 1 is a perspective view of a dental syringe according to an embodiment of the present invention.

In the following, a dental syringe according to an embodiment of the present invention is described with reference to the accompanying drawings.

The dental syringe according to the present embodiment includes a syringe body 1 having a discharge port 1a arranged at its front end and a plunger insertion port 1b arranged at its rear end. Note that in a case where the syringe body 1 is to be filled with a photopolymerization dental material, the syringe body 1 preferably has light shielding properties. Also, the syringe body 1 may be transparent or translucent so that its interior may be perceived. In the dental syringe according to the present embodiment, dental material is injected into the syringe body 1 from the discharge port 1a.

The dental syringe of the present embodiment also includes a plunger 2 that is inserted into the syringe body 1 from the plunger insertion port 1b, and an O-ring 3 that is mounted in an engagement groove 2a formed along a circumferential direction of a front end portion of the plunger 2. The O-ring 3 is arranged to be held in contact with an outer face of the engagement groove 2a and an inner face 1c of the syringe body 1.

The engagement groove 2a of the plunger 2 includes a shallow groove 2aa arranged at the front end side and a deep groove 2ab arranged at the rear end side. First, the shallow groove 2aa at the front end side is arranged such that when dental material starts to be injected into the syringe body 1 from the discharge port 1a and the plunger 2 moves toward the rear end side, the O-ring 3 stops the plunger 2 and restricts its movement within the syringe body 1. Further, the shallow groove 2aa is arranged such that after residual air is discharged toward the rear end side of the syringe body 1 from a gap formed between the O-ring 3 and the syringe body 1 and/or a gap formed between the O-ring 3 and the plunger 2, the O-ring 3 is held in contact with the inner face of the syringe body 1 with a strength that allows the plunger 2 to be pushed by the dental material that has been injected from the discharge port 1a of the syringe body 1 and moved along with the O-ring 3 toward the rear end side. Also, the deep groove 2ab at the rear end side is arranged such that when an end portion at the rear end side of the plunger 2 is pushed by a finger to discharge the dental material injected into the syringe body 1 from the discharge port 1a of the syringe body 1, the O-ring 3 is moved from the shallow groove 2aa to the deep groove 2ab.

Figure 2:
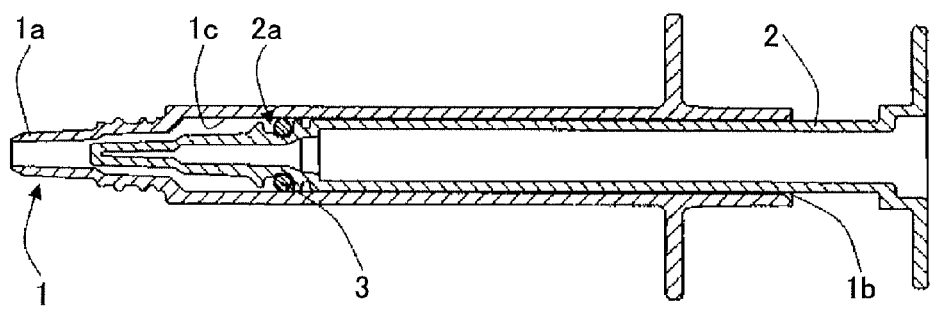
FIG. 2 is a cross-sectional view of the dental syringe of FIG. 1 in a state where a plunger is inserted into a syringe body.

To fill the above dental syringe according to the present embodiment with dental material, first, starting from a state as illustrated in FIG. 1, the plunger 2 is inserted through the plunger insertion port 1b at the rear end of the syringe body 1. When the plunger 2 is pushed toward the front end side, the O-ring 3 that is mounted in the engagement groove 2a of the plunger 2 and is held in contact with the outer face of the engagement groove 2a and the inner face 1c of the syringe body 1 resists movement, and as a result, the O-ring 3 is positioned in the deep grove 2ab of the engagement groove 2a as illustrated in FIG. 2.

Figure 3:
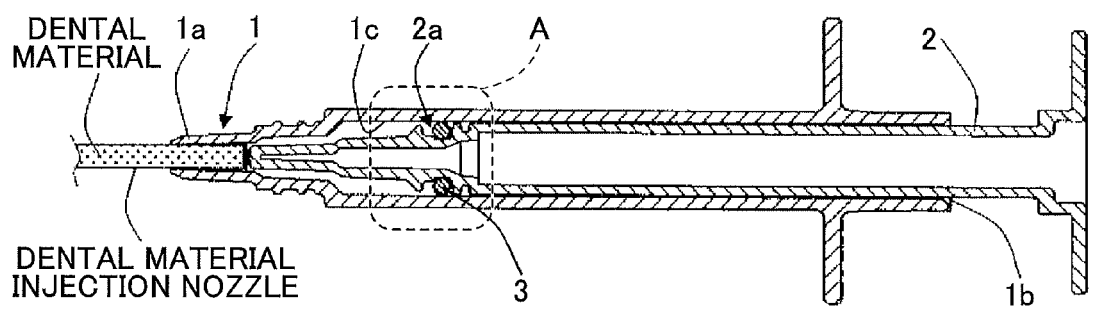
FIG. 3 is a cross-sectional view of the dental syringe of FIG. 2 in a state where a dental material injection nozzle is inserted into a discharge port of the syringe body.
Figure 4:
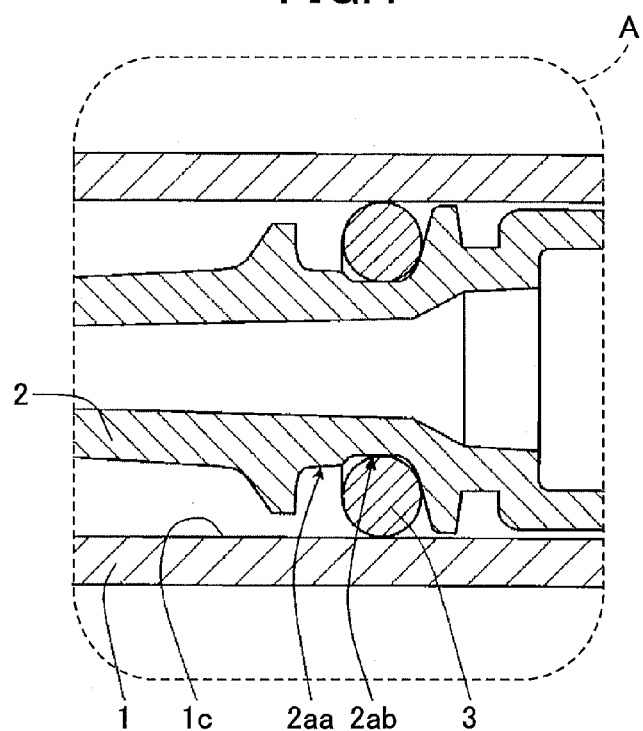
FIG. 4 is an enlarged cross-sectional view of a portion A of FIG. 3.

Then, for example, a dental material injection nozzle may be fitted firmly into the discharge port 1a of the syringe body 1 (see FIG. 3) or externally fitted over the discharge port 1a of the syringe body 1, and dental material may be injected into the syringe body 1 through the dental material injection nozzle. In this way, the dental material may be reliably injected into the syringe body 1 without allowing additional air to be introduced into the syringe body 1.

Figure 5:
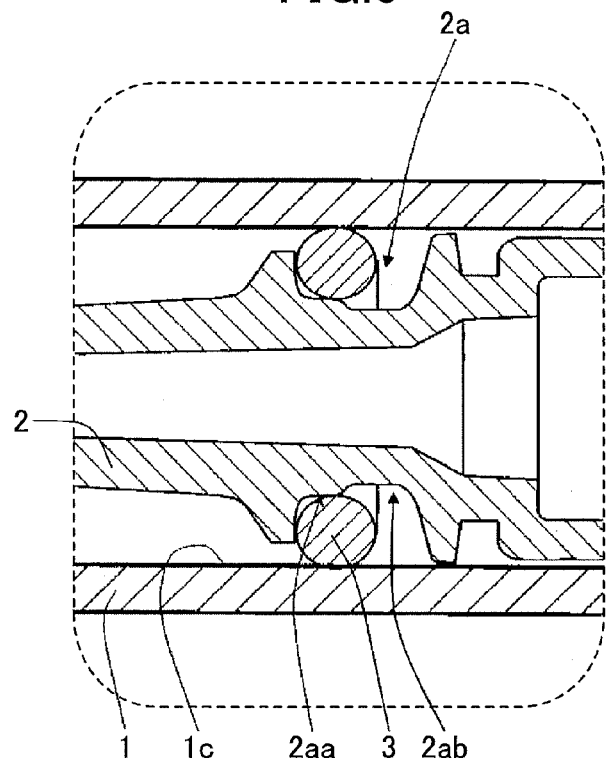
FIG. 5 is an enlarged cross-sectional view of the dental syringe in a state where dental material is injected to cause a plunger to move toward a rear end side from the state illustrated in FIG. 4 and an O-ring to be mounted in a shallow groove relatively positioned toward a front end side of an engagement groove.
Figure 6:
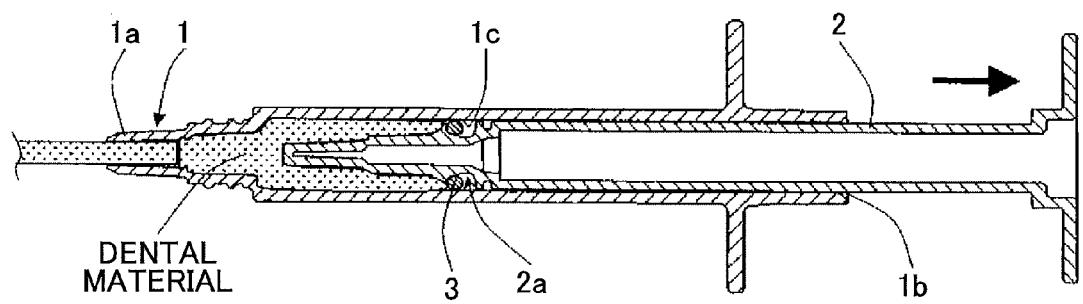
FIG. 6 is a cross-sectional view of the dental syringe in a state where residual air is discharged from the state illustrated in FIG. 5 and the injected dental material moves the plunger along with the O-ring toward the rear end.
Figure 7:
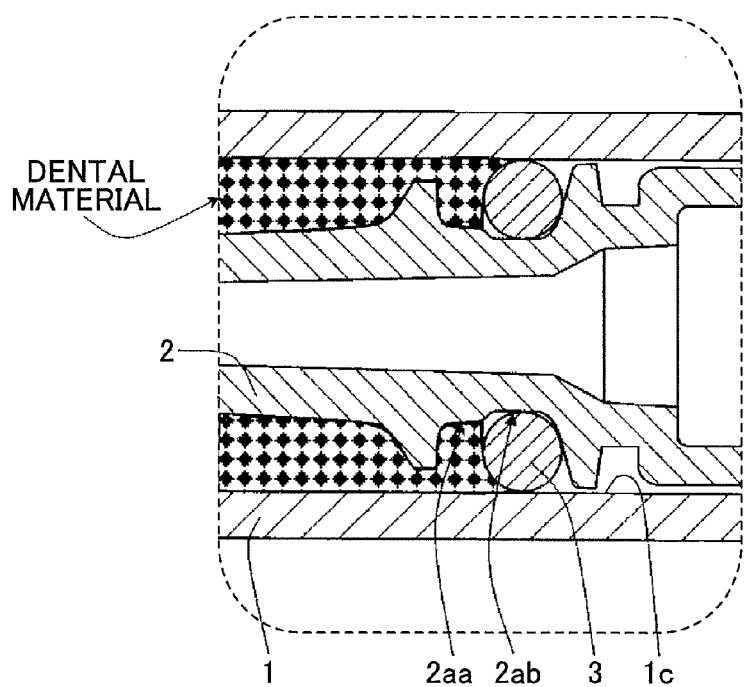
FIG. 7 is an enlarged cross-sectional view of the dental syringe in a state where a rear end portion of the plunger is pushed to discharge dental material from the discharge port of the dental syringe according to an embodiment of the present invention.

When the dental material starts to be injected in the above-described manner, the plunger 2 is pushed toward the rear end side by residual air within the syringe body 1. However, as illustrated in FIG. 5, the O-ring 3 that is held in contact with the outer face of the engagement groove 2a and the inner face 1c of the syringe body 1 resists movement, and as a result, the O-ring 3 is positioned in the shallow grove 2aa of the engagement groove 2a and is tightly held between the outer face of the engagement groove 2a and the inner face 1c of the syringe body 1. In this case, a large load is applied to the plunger 2 and movement of the plunger 2 is restricted.

By using the dental material injection nozzle that is fitted into or over the discharge port 1a of the syringe body 1 as described above, the dental material may be injected at a high pressure. In this way, the residual air may be reliably discharged toward the rear end side of the syringe body 1 from gaps formed around the O-ring 3, for example. Further, after the residual air is discharged, the dental material may flow toward the front end side of the plunger 2 at a high pressure such that the plunger 2 with the O-ring 3 may be pushed with a strong force toward the rear end of the syringe body 1.

In the case of actually using the dental syringe according to the present embodiment having the dental material injected in the syringe body 1, although not shown, a cap that is mounted in the discharge port 1a of the syringe body 1 may be removed, for example, and the rear end of the plunger 2 may be pushed toward the discharge port 1a to move the plunger 2 toward the discharge port 1a. In turn, the O-ring 3 that is held in contact with the outer face of the engagement groove 2a and the inner face 1c of the syringe body 1 resists movement, and as a result, the O-ring 3 is positioned in the deep groove 2ab of the engagement groove 2a.

When the O-ring 3 is positioned in the deep groove 2ab, the O-ring 3 is not held so tightly in contact with the outer face of the engagement groove 2a and the inner face 1c of the syringe body 1. Thus, a user may be able to easily discharge the dental material.

DESCRIPTION OF THE REFERENCE NUMERALS 1 syringe body
1a discharge port
1b plunger insertion port
1c inner face
2 plunger
2a engagement groove
2aa shallow groove
2ab deep groove
3 O-ring

The invention claimed is:

1. A dental syringe comprising:
a syringe body including a discharge port arranged at a front end and a plunger insertion port arranged at a rear end;
a plunger to be inserted into the syringe body from the plunger insertion port, the plunger having a front end, which is positioned towards the front end of the syringe body, a rear end, which is positioned towards the rear end of the syringe body, and an engagement groove, which is formed around a periphery of a front end portion of the plunger and is oriented in a direction orthogonal to the direction of the longitudinal axis of the plunger; and
an O-ring to be mounted in the engagement groove, and held in contact with a bottom face of the engagement groove and an inner face of the syringe body;
wherein the engagement groove of the plunger is defined by a front wall provided towards the front end of the plunger with respect to the bottom face of the engagement groove, a rear wall provided towards the rear end of the plunger with respect to the front wall and on an opposite edge of the bottom face of the engagement groove in a longitudinal direction of the plunger, and the bottom face having a stepped profile in which a shallow groove portion is formed towards the front end of the plunger and a deep groove portion is formed towards the back end of plunger, and
wherein the engagement groove is configured such that
a perimeter of the plunger at the deep groove portion is smaller than the perimeter of the plunger at the shallow groove portion;
when a dental material is injected into the syringe body through the discharge port, the plunger is moved toward the rear end of the syringe body and the O-ring engages with the shallow groove portion, thereby stopping the plunger from moving within the syringe body, and air in the syringe body is discharged toward the rear end side of the syringe body between the O-ring and either of the syringe body or the plunger, and after the air in the syringe body has been discharged, the shallow groove portion holds the O-ring in contact with the inner face of the syringe body with a strength that allows the plunger to be pushed and moved along with the O-ring toward the rear end of the syringe body by the dental material injected through the discharge port; and
when an end portion at the rear end side of the plunger is pushed to discharge the dental material from the syringe body through the discharge port, the O-ring is moved from the shallow groove portion to engage the deep groove portion.

2. The dental syringe according to claim 1, wherein the O-ring has a substantially circular cross-section.

* * * * *